United States Patent
Desilets et al.

(10) Patent No.: US 9,180,314 B2
(45) Date of Patent: *Nov. 10, 2015

(54) APPARATUS AND METHODS FOR THE DESTRUCTION OF ADIPOSE TISSUE

(71) Applicant: LIPOSONIX, INC., Hayward, CA (US)

(72) Inventors: Charles S. Desilets, Mukilteo, WA (US); Cameron Pollack, Sammamish, WA (US)

(73) Assignee: LIPOSONIX, INC., Bothell, WA (US)

( * ) Notice: Subject to any disclaimer, the term of this patent is extended or adjusted under 35 U.S.C. 154(b) by 375 days.

This patent is subject to a terminal disclaimer.

(21) Appl. No.: 13/674,546

(22) Filed: Nov. 12, 2012

(65) Prior Publication Data

US 2013/0072825 A1    Mar. 21, 2013

Related U.S. Application Data

(63) Continuation of application No. 12/559,239, filed on Sep. 14, 2009, now Pat. No. 8,343,051, which is a continuation-in-part of application No. 11/414,080, filed on Apr. 27, 2006, now Pat. No. 7,857,773, which is a continuation-in-part of application No. 11/026,519, filed on Dec. 29, 2004, now Pat. No. 7,993,289.

(60) Provisional application No. 61/097,205, filed on Sep. 15, 2008, provisional application No. 60/676,197, filed on Apr. 29, 2005, provisional application No. 60/553,958, filed on Mar. 18, 2004.

(51) Int. Cl.
*A61H 1/00* (2006.01)
*A61N 7/00* (2006.01)
*A61B 8/08* (2006.01)
*A61N 7/02* (2006.01)

(52) U.S. Cl.
CPC ............. *A61N 7/00* (2013.01); *A61B 8/0858* (2013.01); *A61N 7/02* (2013.01); *A61N 2007/0008* (2013.01)

(58) Field of Classification Search
CPC ................................. A61N 7/02; A61N 7/00
USPC ............................................................ 601/3
See application file for complete search history.

(56) References Cited

U.S. PATENT DOCUMENTS

2004/0039312 A1*  2/2004  Hillstead et al. .................. 601/2

* cited by examiner

*Primary Examiner* — Tse Chen
*Assistant Examiner* — Hien Nguyen
(74) *Attorney, Agent, or Firm* — Thompson Hine LLP

(57) ABSTRACT

Methods and apparatus are described for modifying unwanted tissue for cosmetic reasons. The methods provide a non-invasive manner to perform body contouring by destroying adipose tissue while simultaneously causing collagen contraction in a single procedure so that as destroyed tissue is removed from a treatment volume, the volume shrinks gradually to maintain the skin tone of the treatment area. The procedure may involve multiple treatments to the same treatment area or location.

18 Claims, 14 Drawing Sheets

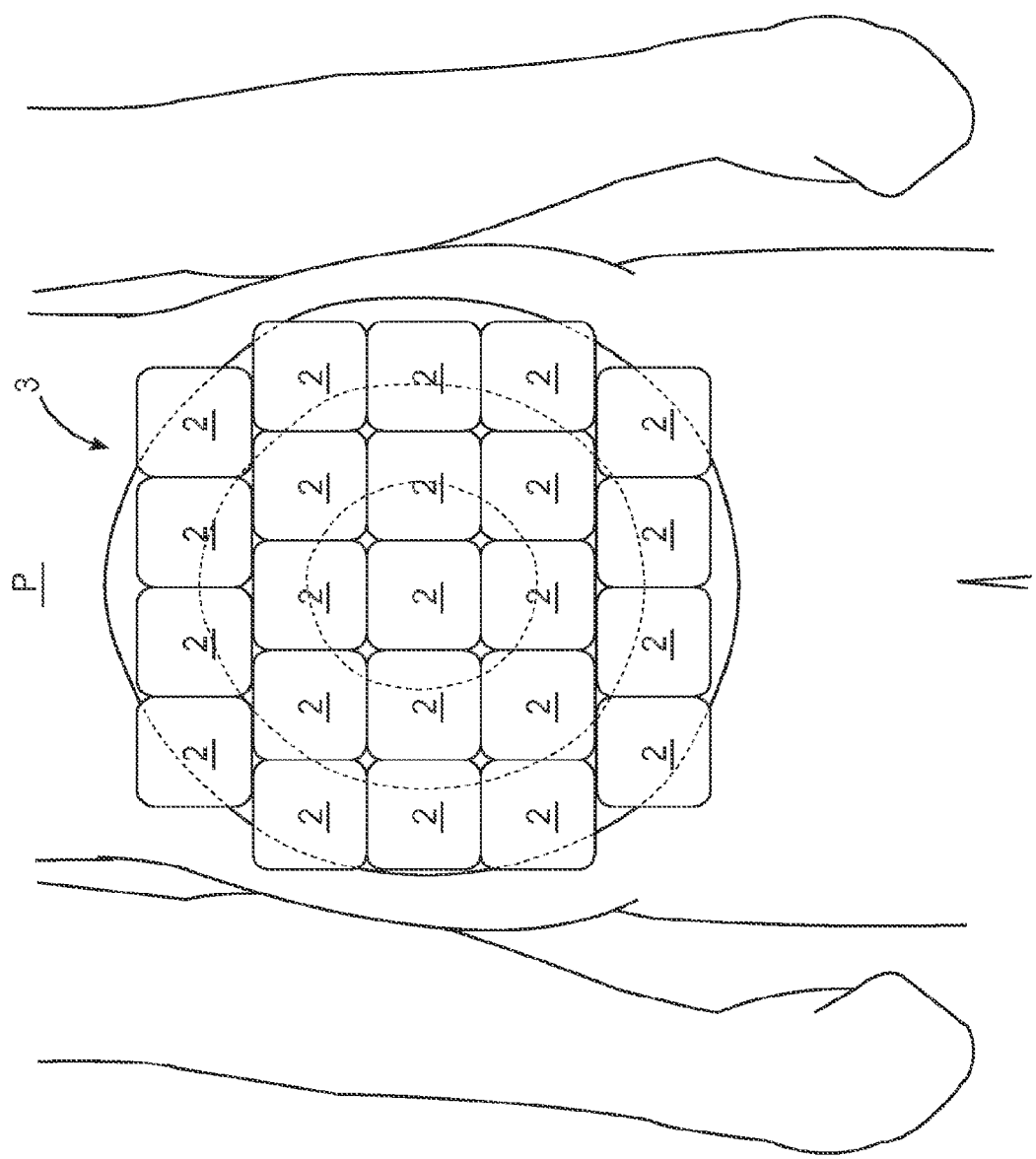

APPARATUS AND METHODS FOR THE DESTRUCTION OF ADIPOSE TISSUE

CROSS-REFERENCES TO RELATED APPLICATIONS

This application is a continuation of application Ser. No. 12/559,239, filed Sep. 14, 2009, which claims the benefit of Provisional Application No. 61/097,205, filed Sep. 15, 2008, and which is continuation-in-part of application Ser. No. 11/414,080, filed Apr. 27, 2006 and issued as U.S. Pat. No. 7,857,773 on Dec. 28, 2010, which (1) claims the benefit of Provisional Application 60/676,197, filed Apr. 29, 2005 and (2) is also a continuation-in-part of U.S. application Ser. No. 11/026,519, filed Dec. 29, 2004 and issued as U.S. Pat. No. 7,993,289 on Aug. 9, 2011, which claims the benefit of Provisional Application No. 60/533,958, filed Dec. 30, 2003. The full disclosure of each of these applications is hereby incorporated herein by reference in its entirety.

BACKGROUND OF THE INVENTION

The present invention relates to using ultrasound apparatus and methods for the noninvasive modification of adipose tissue.

DESCRIPTION OF THE PRIOR ART

Body sculpting has developed into a highly sought after procedure for restoring people to a leaner, trimmer physique. The field of cosmetic surgery has ballooned considerably with developments in both tools and techniques. One of the more popular for quick body sculpting is liposuction.

Liposuction is a method of body contouring that can dramatically improve the shape and contour of different body areas by sculpting and removing unwanted fat. In the United States, more than 400,000 liposuction procedures are performed annually. Recent innovations and advances in the field of liposuction include the tumescent technique and an ultrasonic assisted technique. Traditional liposuction was done by making small incisions in desired locations, then inserting a hollow tube or cannula under the skin in the fat layer. The cannula is connected to a vacuum and the fat is vacuumed out. This procedure indiscriminately removed fat, connective tissue, blood vessels and nerve tissue. The procedure caused bleeding, bruising, trauma, and blood loss; the combination of which restricts the amount of fat that can be removed safely in any given procedure.

The Tumescent technique allows for removal of significantly more fat during the operation with less blood loss. Tumescent liposuction involves injecting saline and adrenalin solution before suctioning. A cannula is again used with a suction device to remove fat. This procedure reduces the bleeding of traditional liposuction. However the procedure still removes a significant amount of non-fat tissue.

A more refined liposuction technique is Ultrasound Assisted Lipoplasty (UAL). UAL is similar to the Tumescent technique, but adds a cannula (or probe) vibrating at ultrasonic frequencies. This vibration disrupts the near volume fat cells and essentially liquefies them for easy removal. UAL uses a low power suction and draws the fat material only in the near vicinity of the cannula tip. This technique is more refined and gentle to the tissue, there is less blood loss, less bruising, less pain, and a significantly faster recovery. All liposuction techniques are invasive and present risks of infection and surgery risks to the patients who undergo these procedures.

Furthermore, once the underlying tissue is removed, the skin may become baggy or loose. To combat loose folds of skin or sagging of skin tissue, a patient may elect to have the extra skin removed (by undergoing a skin excision operation) or elect a skin tightening procedure.

In addition to these invasive forms of liposuction, there are numerous other techniques in the prior art for treating unwanted fat (adipose tissue). These techniques, methods and compositions include, but are not limited to; creams, lotions, garments, massage tools and techniques, therapy procedures involving lasers, RF or ultrasound equipment, general surgery, medication and a host of "home remedies."

Unfortunately none of these procedures provide a one step solution for a patient. The norm is for a patient to undergo multiple treatments, sometimes for the same "trouble spot" on the body, before the patient is satisfied with the results. Techniques and instruments of the prior art are designed for particular applications and operate within parameters specific to one desired outcome.

Thus there remains a need for a single solution to the multiple step problem of either removing or reducing unwanted tissue volume while simultaneously providing for improved cosmetic appearance without the need for secondary or follow on procedures.

There is also a need for a cost effective solution to provide for a simple, quick and effective manner to achieve the desired objective or producing a viable body sculpting procedure in one simple procedure.

BRIEF SUMMARY OF THE INVENTION

Thus it is an objective of the present invention to provide a method and apparatus that can combine the effects of various cosmetic procedures into a single non-invasive procedure that will eliminate or greatly reduce the need for additional procedures.

It is another objective of the present invention to provide a means for controlling the amount of energy needed to treat a problem site depending on the patient and treatment volume.

These and other objectives are achieved through the use of a HIFU ultrasound apparatus and methods for tissue modification.

In a first embodiment there is a method of modifying tissue using high intensity focused ultrasound. The method comprises determining a volume of adipose tissue to be treated, identifying a corresponding surface area of skin over the volume of adipose tissue, moving a HIFU therapy transducer over the surface of the skin and applying therapeutic ultrasound energy into the volume of adipose tissue so that a plurality of cells of tissue necrosis and denatured collagen fibrils are produced.

Alternatively the method may include marking the patient's skin surface to create contour lines and/or guidelines for the HIFU therapy transducer. The motion of the transducer may be continuous or discontinuous. The application of therapy ultrasound energy may be done while the transducer is moving or between segments of movement depending on the desired energy distribution in the volume of adipose tissue. HIFU energy is desirably focused in the volume of adipose tissue to raise the temperature to a level where the adipose tissue is destroyed (or no longer viable) and the collagen fibrils are permanently denatured.

In another embodiment of the present invention, there is an apparatus for the delivery of HIFU energy into a patient. The apparatus having at least one ultrasound transducer adapted for being moved while applying therapy and being capable of depositing an energy flux (EF) greater than 35 J/cm², typically in the range from 35 J/cm² to 460 J/cm², wherein EF is determined by the formula:

$$[p \times (l/v) \times (dc) \times (nl)]/(sa)$$

wherein p=power, l=line length, v=velocity, dc=duty cycle, nl=number of lines, and sa=scanned area.

Preferably, the apparatus is adapted to deposit sufficient ultrasonic energy to produce an EF value greater than 109 J/cm². Additional embodiments and equivalents will be clear upon a detailed study of the following description.

BRIEF DESCRIPTION OF THE DRAWINGS

FIG. 11 shows a mosaic of treatment sites used to cover a treatment area.

DETAILED DESCRIPTION OF THE INVENTION

Figure 1:
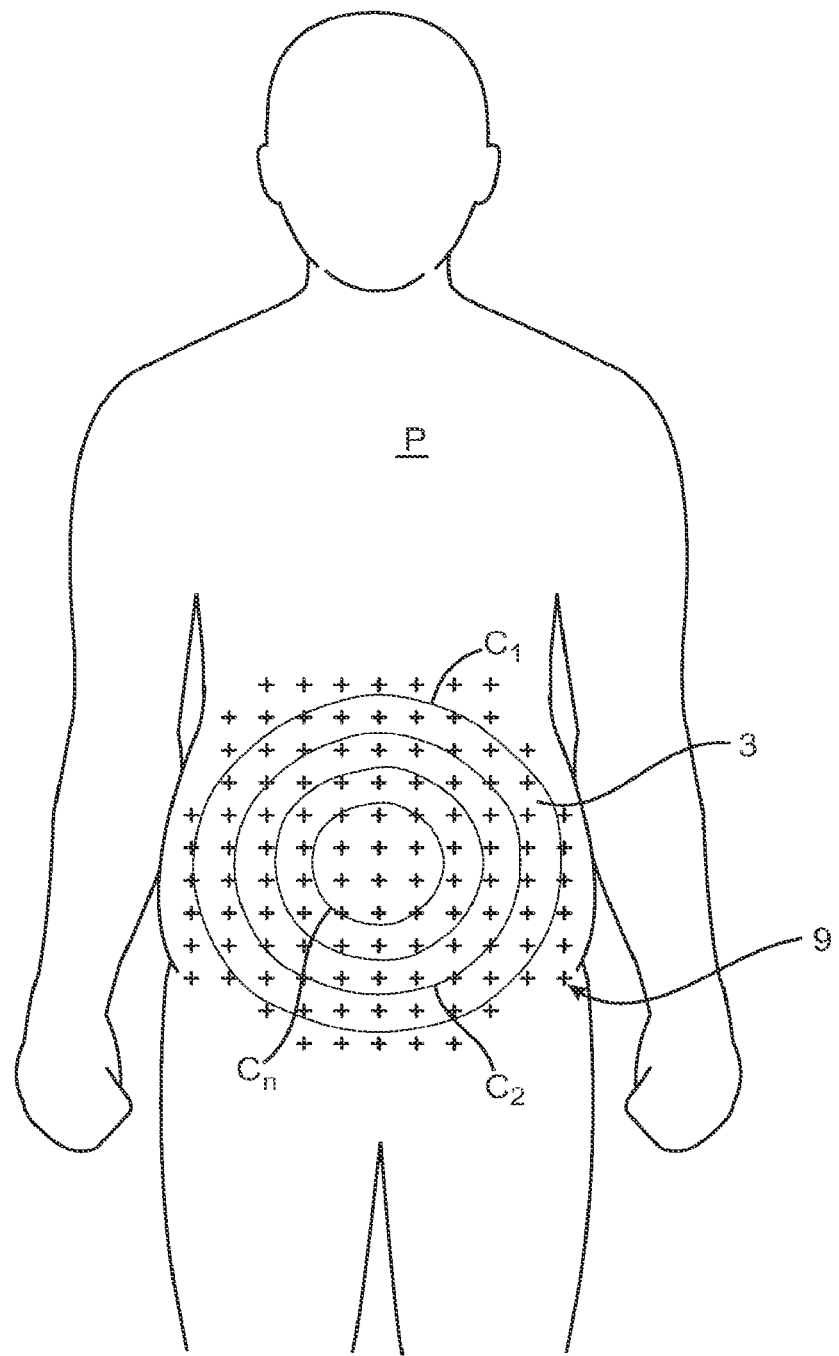
FIG. 1 shows contour and gridlines on a patient.

It should be understood on reviewing the present disclosure that the figures and drawing provided herein are illustrations only. Items shown in these drawings are not intended to be to scale with respect to any key or legend, nor to scale within each drawing. The illustrations may exaggerate particular elements expressly for the purpose of illustrating the element and assisting in the understanding of the accompanying specification.

Methods to address the various issues of patient concern when looking for a non-invasive alternative to liposuction are now described. In one embodiment there is a method of modifying tissue using high intensity focused ultrasound. The method comprises the steps of determining a volume of adipose tissue to be treated, identifying a corresponding surface area of skin over the volume of adipose tissue; and moving a HIFU therapy transducer on the surface area of skin, and applying therapeutic ultrasound energy into the volume of adipose tissue so that a plurality of cells or pockets of tissue necroses and denatured collagen fibrils are produced.

Determining a volume of adipose tissue to be treated is similar to the pretreatment procedures used by cosmetic surgeons prior to a liposuction procedure. A manual pinch test or caliper test can be used by a trained physician to determine if a patient has sufficient adipose tissue at a particular site to warrant a liposuction procedure. The safety measure and standard used by such a test can also satisfy the minimum requirements of a HIFU procedure such as described herein. Alternatively, a physician may use an imaging instrument such as a diagnostic ultrasound device, an MRI device, or a simple A-line scanner to determine if there is sufficient adipose tissue depth in a desired area to be treated using HIFU energy.

While the depth of the adipose tissue should be sufficient to allow the focal zone of the HIFU transducer to be safely in the adipose tissue with some margin of safety both above and below the focal point of the transducer, it should be understood that varying the focal depth of the transducer, as well as the shape and focus of the transducer can allow for more precise control over the delivery of HIFU energy, while simultaneously reducing the clearance zones needed for safe operation. That is to say a highly focused transducer provides sufficient control and focus to allow for a reduced safety clearance.

Once the volume of tissue is identified, the physician should determine the corresponding surface area over the volume that can be treated. Once again, borrowing from existing techniques in liposuction, the physician may proceed directly to treating the patient using a HIFU transducer, or she can create one or more contour lines as part of the treatment planning phase of an ordinary liposuction procedure. During this step the physician may draw or otherwise indicate on a patient skin surface, a region that can safely be treated using a HIFU transducer. Pens or markers may be used to create these contour lines.

Next is the application of HIFU energy into the volume of adipose tissue. A HIFU transducer is moved over the surface area identified above. The transducer emits energy to the focal zone in sufficient strength (power) and intensity (pressure) to cause cellular necrosis and collagen fibril denaturing. Depending on the pulse repetition frequency and velocity that the transducer is moving, a plurality of discrete treatment cells will be produced. Desirably each treatment cell will absorb sufficient energy from the transducer to cause cellular necrosis of all cells in the focal zone, as well as collagen denaturing in the same region. The volume of tissue affected at the focal zone of the transducer is the lesion field 630 (FIG. 3A-5B). The volume around the lesion field 630 where adipose tissue is destroyed and/or collagen fibrils are denatured is the halo field 6. If the transducer is moved in a continuous manner such that a single linear lesion field is formed along the path or axis of motion, the lesion field is said to be contiguous, or a contiguous lesion field 630c. Similarly the halo field 6 may be a contiguous halo field 6c. A volume of over lapping lesion field produced from more than one scan line (such as an intersection) forms a cooperative lesion field, while overlapping halo fields are referred to as cooperative halo fields. Overlapping halo fields may be produced by operating the HIFU transducer in a manner such that scan lines intersect one another, or run parallel close enough so their corresponding halo zones overlap. The sum of the tissue volume of the various lesion fields and halo fields produced during a therapy procedure comprises the treatment area 3.

In accordance with an embodiment, the application of HIFU energy into the volume of adipose energy may involve multiple treatments at the same location. In such an embodiment, the cumulative strength (power) and intensity (pressure) is sufficient to cause cellular necrosis and collagen fibril denaturing. This cumulative effect permits each individual treatment to be of insufficient power and intensity to cause cellular necrosis and collagen fibril denaturing.

Figure 14:
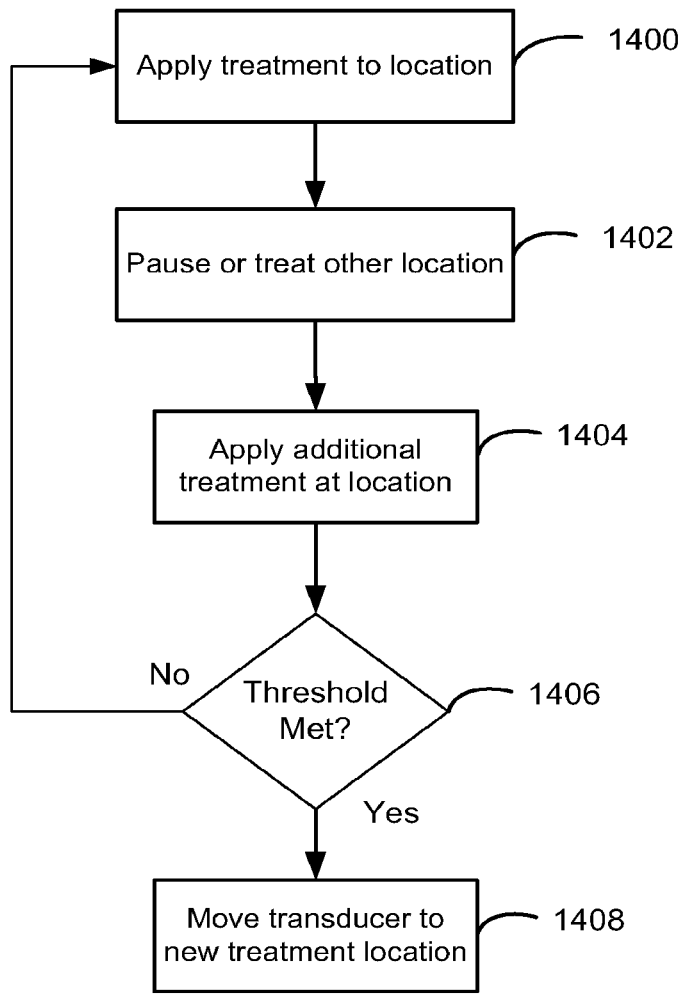
FIG. 14 is a flow chart showing steps for providing multiple treatments to a single location in accordance with an embodiment.

FIG. 14 is a flow chart showing steps for providing multiple treatments to a single location in accordance with an embodiment. Beginning at step 1400, a first application of HIFU energy (i.e., a first treatment) is applied into a particular location in adipose tissue. At step 1402, a pause is taken, in which treatment may be applied to another location. At step 1404, an additional treatment is applied to the same location. At step 1406, a determination is made whether the power of the cumulative treatments is sufficient to cause cellular necrosis and collagen fibril denaturing. If not, the process branches back to step 1400, and a further treatment is applied. If so, the applications at that location may be completed.

It can be understood that such cumulative treatments may be repeated to accumulate even more power, but at a minimum, the accumulation is sufficient to cause cellular necrosis and collagen fibril denaturing. Also, an evaluation need not be done after each treatment (as indicated by step 1406), but instead the number of treatments at a given location may be determined empirically or clinically. It should also be understood that the application of energy to the treatment site may vary from one treatment to another at the same location. For instance if it is desirable to apply a value of X power and/or pressure to a region of tissue, it may be applied in more than one application in which all applications are equal, or in which the sum of the applications is X, but each application is a different fraction of X. Once the desired application of energy is achieved, the transducer is relocated to a new location and the process may be repeated at a different location at step 1408.

The destruction of adipose tissue in the lesion field is not restricted to adipocytes (fat cells) alone. The methods described herein are intended to destroy biological tissue within the focal zone by whatever mechanism the HIFU transducer can produce. Furthermore the thermal energy which radiates from the lesion field destroys the surrounding tissue forming the halo field. This thermal radiation is not intended to be of a particular temperature for selective preservation of any biological material. The temperature in the halo field should be sufficient to destroy the adipose tissue and denature the collagen fibrils. Thus, it is likely that other cells or tissue types within the lesion and halo field will be destroyed.

In one embodiment, the application of HIFU energy may be done in a manner to form a pattern of discrete lesion fields 630 and halo fields 6 within a treatment area 3. In another embodiment, the application of HIFU may be done in a manner that divides the treatment area 3 into a plurality of smaller treatment sites 2, and the sum of the treatment sites 2 produces the desired coverage to form the treatment area 3 (FIG. 11). Alternatively, HIFU energy may be applied in either continuous or discontinuous motion through individual treatment sites 2, or across the entire treatment zone 3. The various treatment sites 2 which form the treatment zone 3 on a patient may be uniform or different in both size of each treatment site 2 within the treatment zone 3, as well as having any mixture of lesion fields 630, contiguous lesion fields 630c, cooperative lesion fields, halo fields 6, contiguous halo fields and cooperative halo fields. In addition, for each treatment site, as described above, multiple treatments may be provided, with the multiple treatments having any of these forms.

Figure 8:
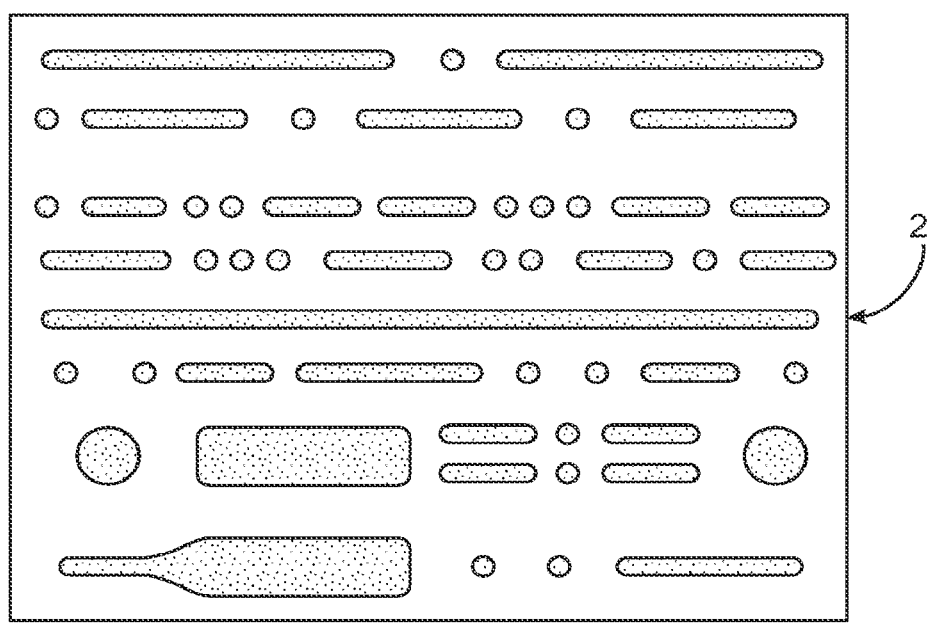

In yet another embodiment of ultrasound application according to the present methods, the transducer may be used to deposit energy and produce lesion fields of varying shapes and sizes. If the transducer is left to reside in a single position (such as using an incremental movement), the transducer may initially create a small lesion field. By allowing the transducer to loiter, thermal energy will build up and radiate out from the lesion field. The transducer may be moved slowly or have higher energy output while moved in a regular movement pattern to produce larger contiguous lesion fields (produce thicker scan lines). By analogy, one may envision the way a fountain pen leaves ink on a page. Just as the nib of a fountain pen allows ink to spread across paper from the point of contact of the nib, so too does thermal energy radiate out from the focal zone of the transducer the longer the transducer is left to loiter over a particular spot of adipose tissue. Some variations of these lesions are shown in FIG. 8. Similar to those scan lines 4, lesion fields 630 and halo field 6 previously described, there are now shown enlarged halo fields. Here the scan line 4 may produce a spot shaped lesion field 630 with a generally spherical shaped halo field 6. Increasing the power broadcast into the tissue may be achieved by moving the transducer slowly, varying the parameters of the transducer, so that more energy radiates from the lesion field into the surrounding tissue, thus producing an enlarged halo field. Similarly, the lesion field itself may also increase in size.

Figure 15:
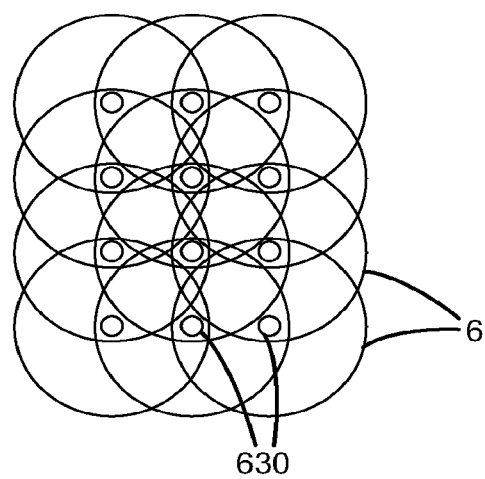
FIG. 15 is a representation of an ultrasound treatment pattern in accordance with an embodiment.

Using the varied sizes along with multiple treatments for a single location allows a number of variations. For example, as shown in FIG. 15, large halo fields may be overlapped so that each location has four halo effects at each lesion field. The system may be arranged so that the cumulative power applied at each lesion field is sufficient to cause cellular necrosis and collagen fibril denaturing.

Figure 4A:
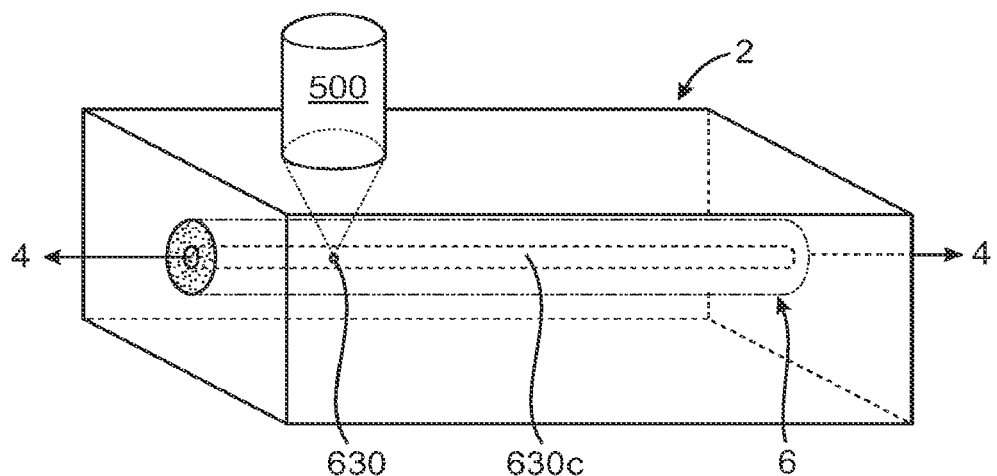
Figure 4B:
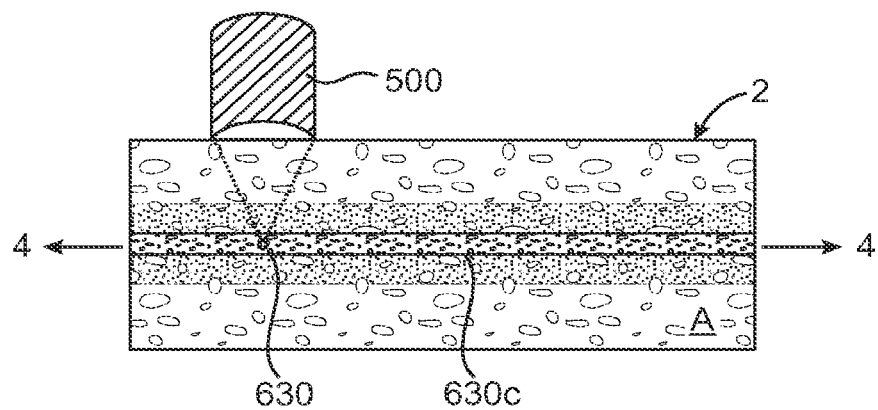

The motion of the transducer over the patient skin can follow any number of patterns. A basic motion is shown in FIG. 4A. Here a transducer 500 is moved in a linear path over the patient skin. The transducer has a focal zone 630 which creates a lesion field. If the transducer is moved in a controlled manner the lesion field formed by the HIFU therapy transducer may form a single, contiguous line of destroyed tissue 630c. The axis of the focal zone in tissue is referred to herein as the scan line 4. Surrounding the scan line 4 is a region of thermal effect desirably raising the local tissue to temperatures sufficient to kill adipose tissue and denature collagen fibrils. This halo field 6 about the scan line 4 represents the volume of tissue which receives sufficient thermal radiation from the lesion field 630, 630c to also be destroyed and denatured. The halo 6 may be large or small depending on how quickly the transducer is moved, and how much power the transducer produces. Here a single scan line 4 is shown within a single treatment site 2 for clarity. A cross section view of a scan line 4 is shown in FIG. 4B.

For multiple treatments at the same location, a scan line may be repeated. Alternatively, scan lines may cross or overlap to provide a desired accumulation.

Figure 3A:
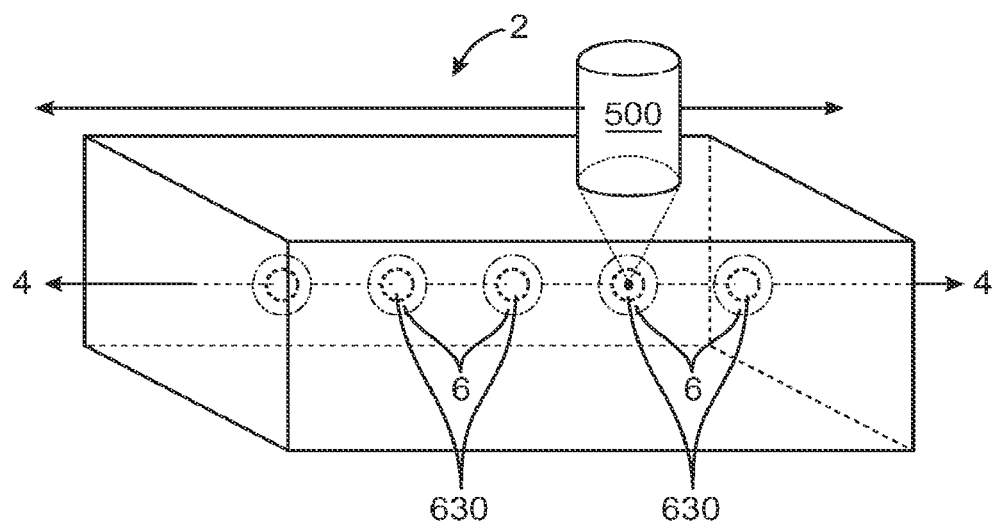
FIGS. 3A-5B illustrate various treatment approaches.
Figure 3B:
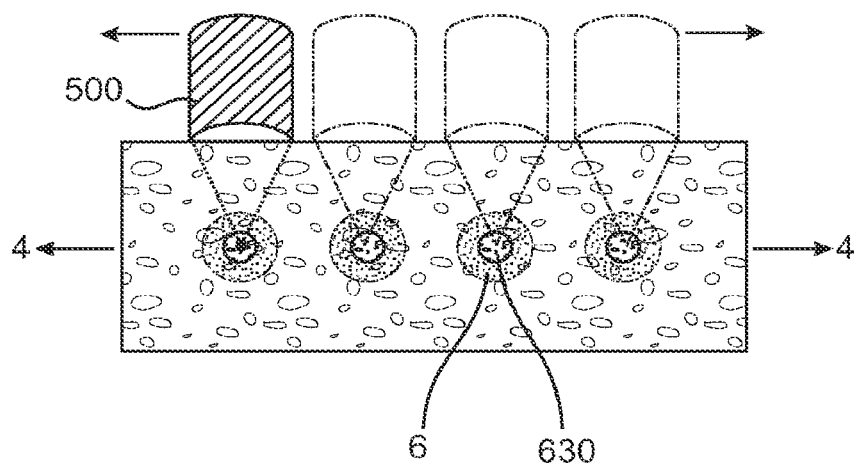

Alternatively, the transducer 500 may be made to produce high intensity pulses or pulse bursts (rapid sequence of discrete pulses) to produce discrete lesions 630 along a scan line 4 (FIG. 3A). In this embodiment, the transducer is desirably moved over the patient skin surface and the transducer is programmed to deliver discrete bursts of HIFU ultrasound energy to produce individual or discrete "cells" of destroyed tissue. The burst of ultrasound energy can produce any variety and number of discrete lesions in the tissue. A halo 6 may also be found surrounding each lesion depending on the operating parameters of the transducer. Again, the pattern of lesion fields and halos are also presented in cross section shown in FIG. 3B.

Figure 5A:
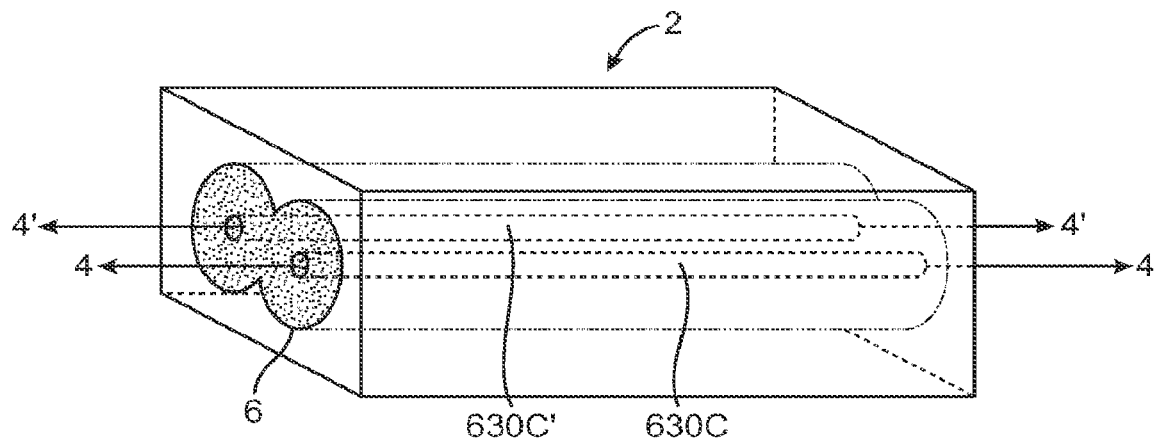
Figure 5B:
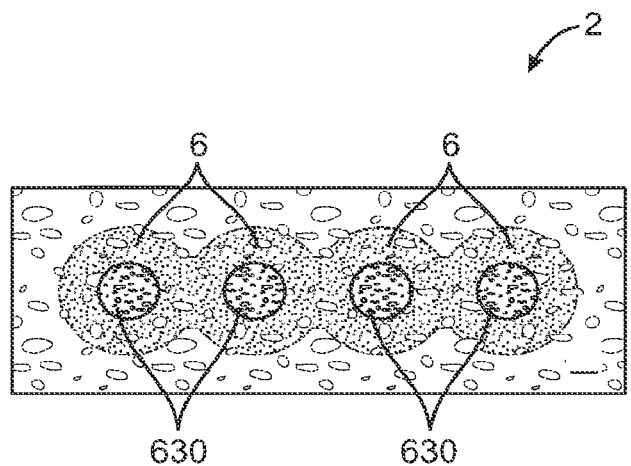

Another embodiment for applying ultrasound energy is illustrated in FIGS. 5A-B. Here two scan lines 4, 4' are shown in close proximity so that the contiguous lesion fields 630c, 630c' are parallel. The halo zone 6 of each scan line run together to form a region of cooperative effect and enlarge the halo zone. Multiple scan lines may be placed side by side to form a large layer of mechanical and thermal effect (FIG. 5B).

For multiple treatments at the same location, individual scan lines may be repeated at the same location, or slightly moved over so as to overlap a previous line. Alternatively or in addition to this arrangement, scan lines may cross or overlap to provide a desired accumulation. A large number of scan lines may be utilized for a treatment area with several overlaps in the scan lines and so that cumulative power at most or all locations is sufficient for cellular necrosis and collagen fibril denaturing. Collagen denaturing can occur at temperatures above 37° C. However denatured collagen at temperatures close to normal body temperature may recover, relax and resume their normal length. Desirably then, collagen in the treatment zone is exposed to temperatures above 37° C. More desirably collagen fibrils in the treatment zone are exposed to temperatures above 46° C. and even more preferably to temperatures above 56° C. The higher the temperature the collagen fibrils are exposed to, the shorter the length of time needed to achieve the desired effect (permanent collagen denaturing for contraction of collagen fibrils). When the exposure is at 46° C., the collagen fibrils need to be incubated at that temperature for at least several minutes, however exposure of collagen fibrils to temperatures near or above 56° C. may be done in less than a few seconds. "Collagen Fibril" refers to the collagen material found in adipose tissue or sub dermal regions where collagen concentration tends to be sparse and used by the body as a lattice connective tissue rather than a major structural component (contrast with regions like the nose, ears, skin or tendons and the like). Contraction of collagen fibrils refers to using thermal energy to denature the collagen and force the collagen fibrils to shorten lengthwise.

Desirably adipose tissue is heated using HIFU energy so the temperature in the lesion field is raised as high as practical and as fast as possible. Parameters of the HIFU transducer may be adjusted to produce the desired fast heating needed to destroy adipose tissue and denature collagen fibrils. Desirably the fast heating is balanced with the volume and dimensions of the adipose tissue to be treated. The longer the transducer remains active on one location, the larger the halo field. Desirably the moving of the HIFU transducer and the applying of therapeutic ultrasound energy do not produce lesion or halo fields which extend beyond the dimensions of the adipose tissue volume.

Although using higher power and pressure produce faster results, using higher power may cause some patient pain. The same or a similar effect may occur, however, by using multiple lower power treatments at a same location so that there is an accumulation of power resulting in a similar treatment.

Additional parameters that affect the size of the lesion and halo fields are those parameters electronically controlled through the transducer, and parameters of the transducer itself. These parameters include (but are not limited to) power, frequency, duty cycle, focus, size (of transducer), and pulse repetition frequency.

Figure 6:
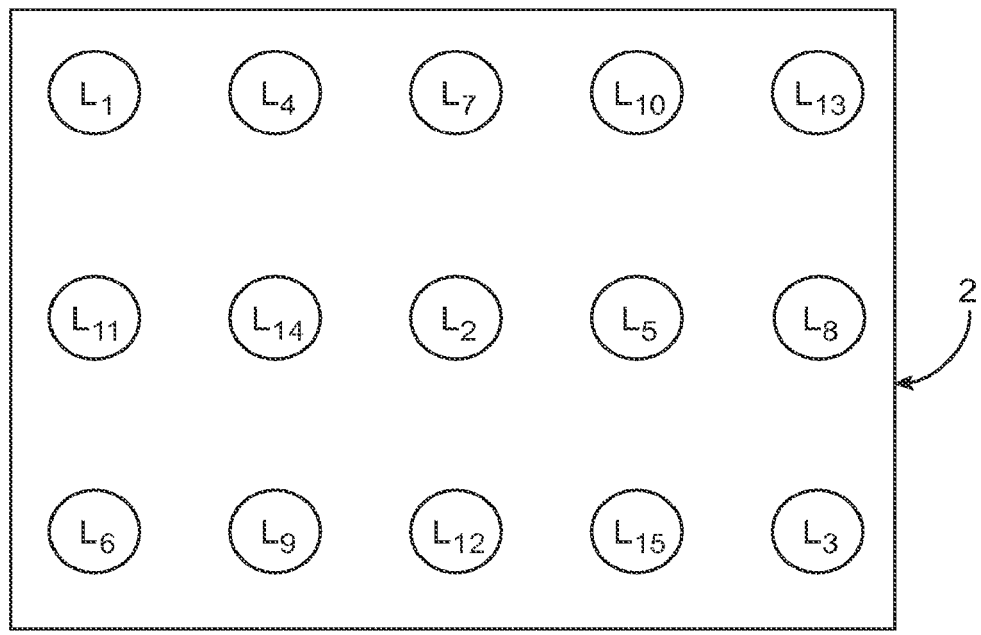
FIGS. 6-8 illustrate various ultrasound treatment patterns.

In some applications, the size of the lesion and halo fields are desirably minimized. This is particularly true where the adipose tissue depth necessitates a tightly controlled lesion and halo field due to proximity of muscle, organs or skin. This can be accomplished by distributing the individual lesion fields within a treatment site apart from each other in both distance and time. If the treatment site is represented by a defined field area 2, then the individual spot lesions may be laid down one at a time in a sequence from $L_1$ to $L_{15}$ (FIG. 6). For multiple treatments at each location, the sequence may be repeated or may be performed in a different order. Here the lesions are temporally separated as well as being spatially separated. This pattern allows for the individual lesions to have a minimum cooperative thermal effect between lesions. The size of each lesion ($L_{1-n}$) may also be controlled by adjusting the parameters of the ultrasound transducer used in the treatment.

Figure 7:
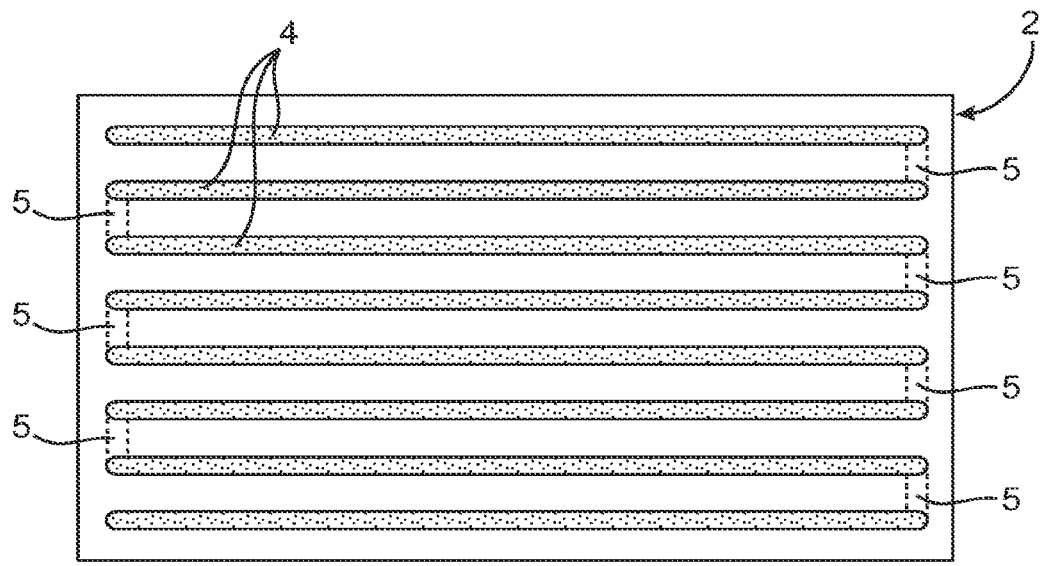

Alternatively, the lesion and halo fields may be maximized by permitting the HIFU transducer to produce contiguous lesion fields and cooperative halo fields. An example of such a maximizing movement scheme is illustrated now in FIG. 7.

In this embodiment, the energy required to produce cellular necrosis and collagen contraction is lessened due to the cooperative effect of having the transducer operate in narrowly spaced treatment lines and in rapid succession of laying down treatment lines near each other in both time and space. Movement of the transducer is desirably machine controlled for uniformity and simultaneous control of the transducer. The transducer can treat patient tissue volume by moving over the surface of the tissue volume in any variety of patterns including, but not limited to, spiral, raster scan, or patterned. Thermal cooperation can be maximized by delivering the ultrasound energy as a contiguous lesion field 630 within the treatment site 2. A raster scan type pattern (FIG. 7) may be used with a relatively close line spacing to provide for a maximum of thermal cooperation to produce a large halo region. The horizontal scan lines 4 may be connected with vertical transit lines 5 where the transducer is active, or the vertical transit lines may be "empty" if the transducer is not active while moving vertically. Likewise the spacing between the horizontal lines 4 may be close together or physically overlapping to provide for the maximum overlap of ultrasound energy. For multiple treatments on a same location, as described above, the raster pattern may be repeated or different crossing or overlapping patterns may be used to provide desired accumulation at each location. Careful planning and consideration in the applying of ultrasound energy in the methods described herein can produce the desired volume of tissue modification in both the amount of adipose tissue destroyed, and collagen denatured.

A balancing of speed (velocity of the focal zone in the tissue being treated) and the power and intensity of the transducer are needed to produce the desired effect. A method of determining the various parameters to use in a tissue modification is now described. In this embodiment, there is a method of reducing adipose tissue volume in a patient using high intensity focused ultrasound. The method comprises the steps of determining a volume of adipose tissue to be treated; marking out a corresponding surface area of skin and applying high intensity focused ultrasound energy to said area in a manner sufficient to induce the gradual destruction of said adipose tissue and denaturing of collagen fibrils, the energy flux being of at least than 35 $J/cm^2$. Operationally the speed of destruction may be quickened by providing higher EF values. By scanning the transducer over a volume of adipose tissue at higher EF values, the amount of time needed to achieve adipose tissue necrosis and collagen fibril denaturing can be reduced. Using EF values between 90 and 225 Joules per square centimeter allow for the desired treatment to be done quickly. Further increasing the EF to higher values also produces viable results under certain conditions, going as high as 460 $J/cm^2$.

Accumulation can provide a desired EF value without the application of high energy flux pulses. For example, two separate treatments, each having 33 $J/cm^2$, may result is an accumulated EF of 66 $J/cm^2$, without having to resort to a treatment exceeding 35 $J/cm^2$. As such, efficacy may be enhanced with greater patient tolerance.

By using a predetermined energy flux value, the transducer can be programmed to consistently and accurately deposit the same amount of energy into each of the lesion fields (also referred to as the focal zone). Through experimentation and analysis, we have found that tissue ablation of adipose tissue and collagen contraction can occur at energy fluxes above 35 joules per square centimeter. Variations in desired outcomes and tissue variations from patient to patient make calling out an exact energy flux figure impossible. However empirical data from multiple study sources suggest the energy flux value, from cumulative or a single treatment, should be greater than 35 joules per square centimeter and are probably most efficacious for the dual purpose of destroying adipose tissue and denaturing collagen fibrils at or above 109 joules per square centimeter.

In a physical embodiment of the present invention, there is an apparatus for the delivery of therapeutic ultrasound energy into a patient. The apparatus having at least one ultrasound transducer adapted for being moved while applying therapy and being capable of depositing an energy flux (EF) greater than 35 J/cm², wherein EF is determined by the formula:

$$[p \times (l/v) \times (dc) \times (nl)]/(sa)$$

wherein p=power, l=line length, v=velocity, dc=duty cycle, nl=number of lines, and sa=scanned area.

The formulation provided provides for a calculation when the transducer is moving continuously while applying ultrasound energy. Alternatively for a treatment program where the transducer is not moving between therapy applications, the EF can be calculated using the following modified EF equation.

$$EF = [(p) \times (t) \times (dc) \times (ns)]/(sa)$$

wherein p=power, t=on-time per lesion, dc=duty cycle, ns=number of lesions, and sa=scanned area.

Variations in the formula can be derived by those skilled in the art to determine the proper calculations for a therapy program having a mixed set of moving and non-moving treatment sites. The therapy controller desirably allows for a wide variation in parameters which a user may manually feed into the therapy controller prior to each application of ultrasound. The therapy controller determines which variables are to be used and weights them accordingly. An example of a medical instrument system for use with the methods described herein is further described in co-pending U.S. patent application Ser. No. 11/027,912 entitled "Ultrasound Therapy Head with Movement Control", the contents of which are hereby incorporated by reference herein in their entirety.

Another example is described in co-pending U.S. patent application Ser. No. 11/026,519 entitled "Systems and Methods for the Destruction of Adipose Tissue" filed on Dec. 29, 2004, the contents of which are hereby incorporated by reference herein in their entirety. The apparatus for the delivery of therapeutic ultrasound energy into a patient has a scan head, suspension device for supporting the scan head, and a therapy controller. The therapy controller is adapted to monitor the position and energy deliver of the scan head. This apparatus may be used to deliver multiple treatments to the same location by having the scan head return multiple times.

Figure 16:
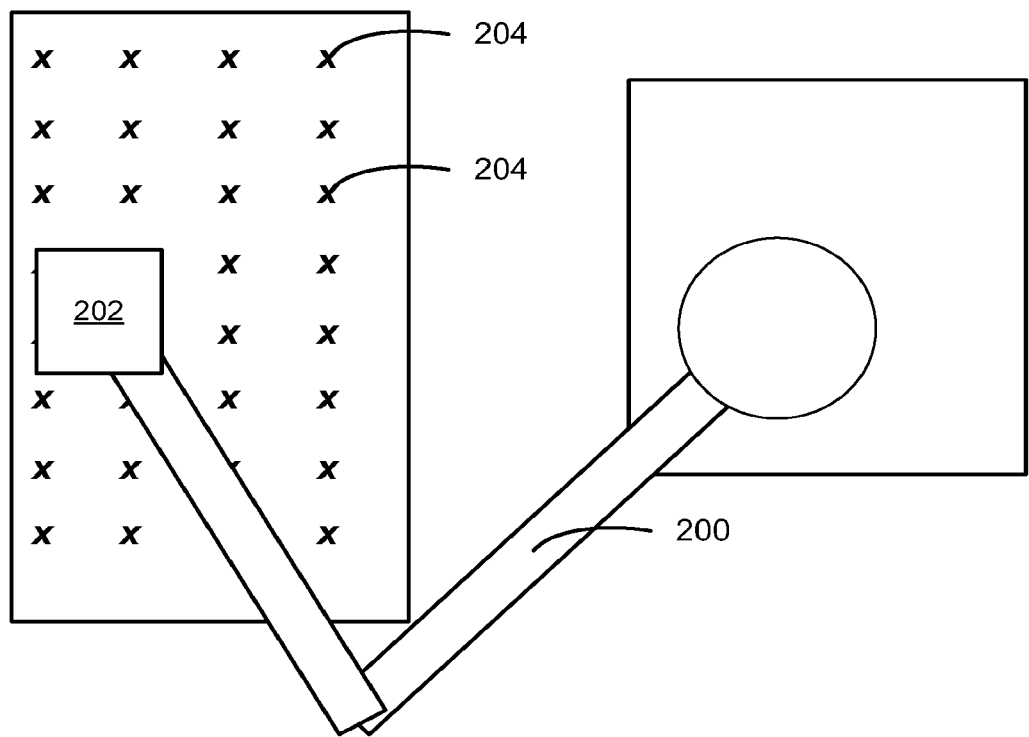
FIG. 16 a block representation of a robot arm apparatus that may be used in a procedure in accordance with an embodiment.

Another example is shown in FIG. 16, where a robot arm 200 moves a scan head 202 over multiple markers, for example on a patient's body. The scanner head 202 may be directed by a physician to the markers, and then instructed to apply a treatment. The robot arm may remember the position, for example using kinematic information, and after the physician has placed the scanner head at each treatment location, return automatically to each of the locations so that multiple treatments may be applied to the each location. Alternatively, the robot may remember a location, for example via kinematics, and count the number of applications applied by a physician. As still another alternative, the scanner head may include optical recognition hardware, and may automatically find a marker and apply a treatment.

The various parameters of the Energy Flux equation can be programmed into the therapy controller. The apparatus may have some parameter data programmed in fixed memory and not adjustable by the user. Some elements may include maximum and minimum settings of the transducer to prevent the apparatus from being operated in an unsafe manner.

A user can provide variables into the system to help the system determine the proper EF to be used during a procedure. For example if the user wishes to increase cooperative heating between scan lines, the scan lines (nl) may be set to a higher value. Alternatively the velocity may be reduced to promote larger halo fields, or the velocity may be increased to decrease halo fields as might be required for regions of adipose tissue which have smaller margins.

Figure 9:
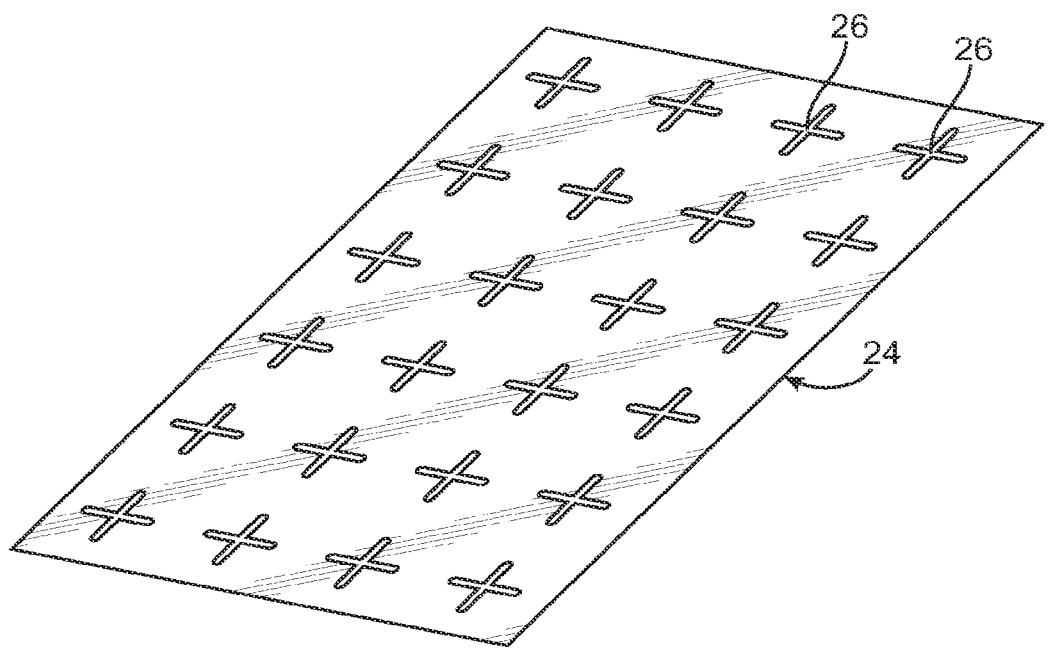
FIG. 9 illustrates a stencil.

A stencil or template 24 can be used to assist a physician in planning the treatment (FIG. 9). The template 24 has a series of apertures 26 in the form of "crosshairs" which can be used to guide the ultrasound transducer during the treatment procedure. The template 24 desirably is created so the apertures match the foot print of the transducer to be used (or therapy device depending on the ultrasound system selected). The template may be used across the skin prior to the creation of contour lines or prior even to the evaluation of the adipose tissue in the target region. Desirably a physician will mark the contour lines and crosshair marks after making the determination of suitable adipose tissue depth in the patients target treatment region.

Figure 2:
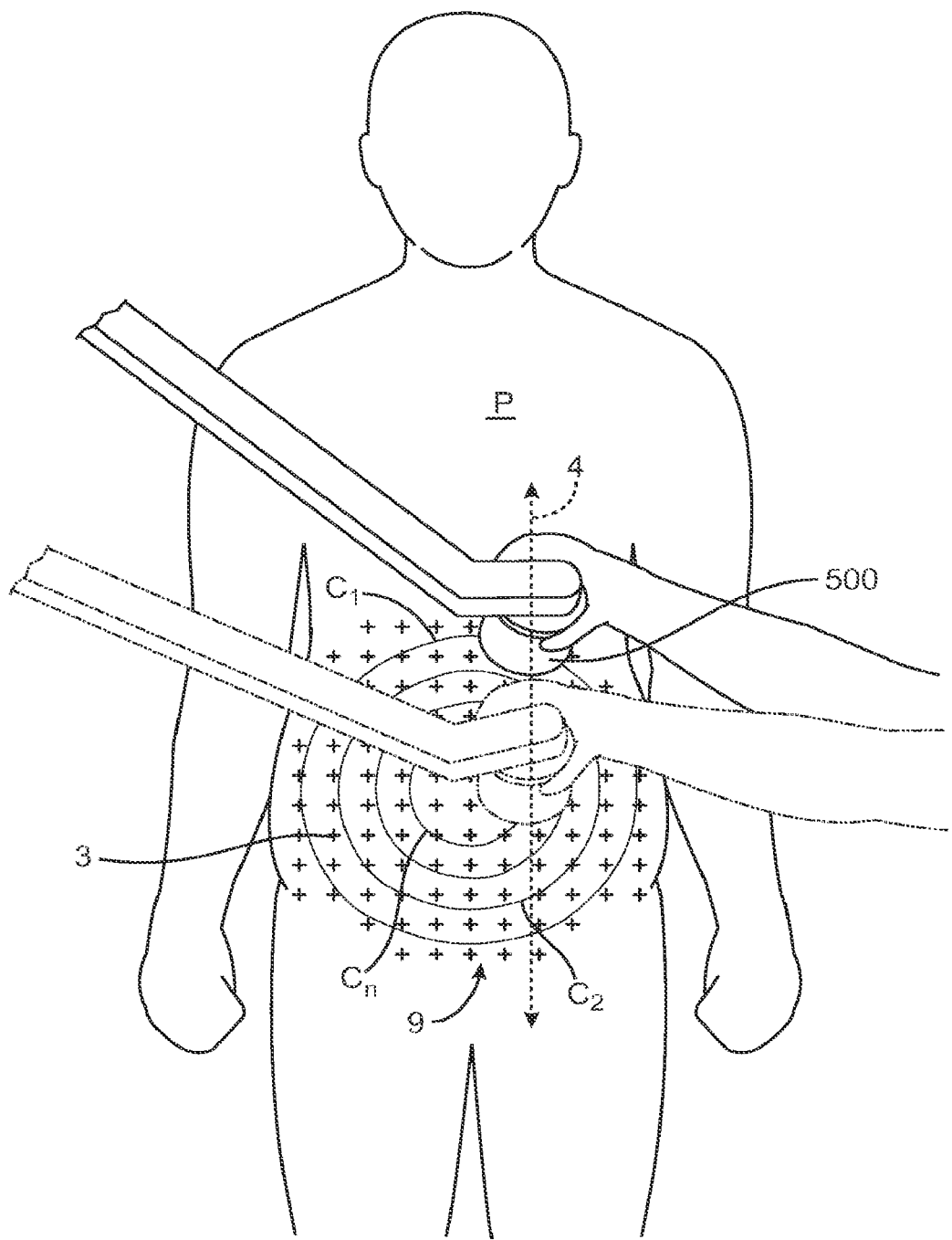
FIG. 2 illustrates the motion of a HIFU treatment device over the patient.
Figure 10:
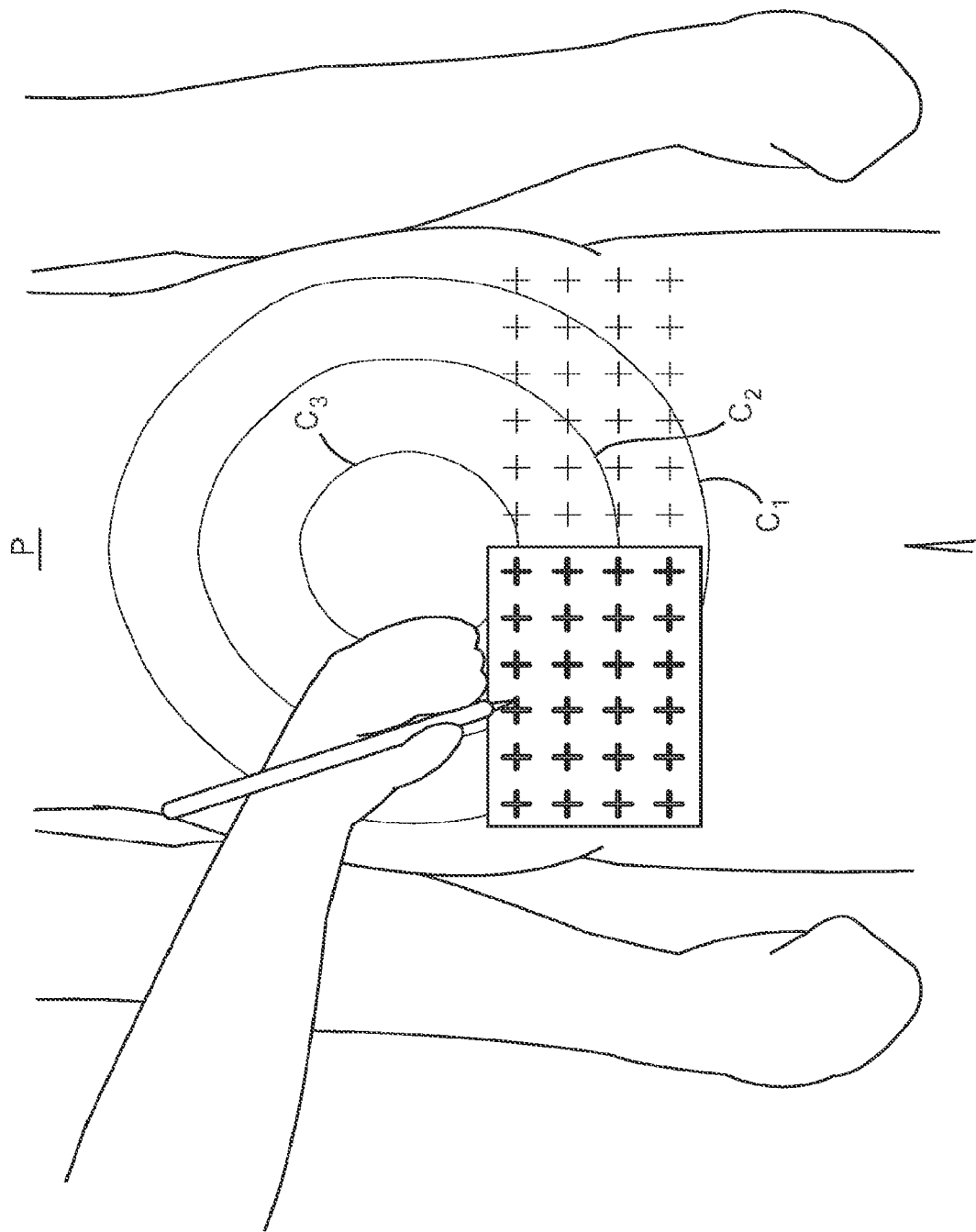
FIG. 10 illustrates the use of a stencil on a patient.

The stencil 24 can be laid across the patient (FIG. 10) and then the crosshairs drawn in using a medical marker. The combination of crosshairs and contour lines shown in FIG. 1 combine to provide visual markers for the safe placement of a HIFU transducer in an ordered fashion (using the guide marks) within a known depth of adipose tissue (using the contour lines). Once the two markings are on the patient, the physician need only line up the ultrasound treatment device with the crosshairs and contour lines (FIG. 2) to produce a mosaic of treatment sites 2 (FIG. 11).

The volume of tissue to be treated can be done using techniques already adopted by physicians in the ordinary practice of procedures like UAL. The physician can use a manual pinch test, calipers or diagnostic ultrasound to determine the depth of the fat tissue to be treated and draw circles around the region to be treated, similar to relief lines on a topographical map. The individual marks from the stencil may be made before the volume is determined, or after. The contour lines representing varying levels of tissue volume, and therapy head land marks overlap to provide the user with a defined safe area to treat, as well as a guide for treatment using the ultrasound therapy head.

Figure 13:
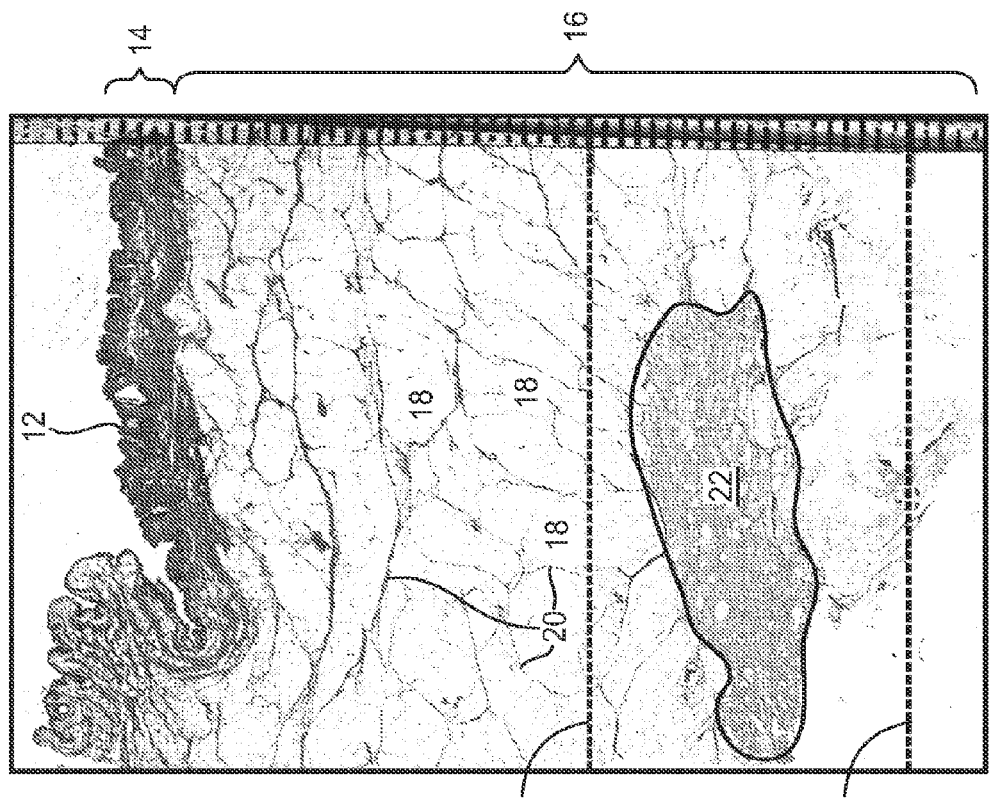
FIGS. 12-13 show histology slides of actual treated tissue.
Figure 12:
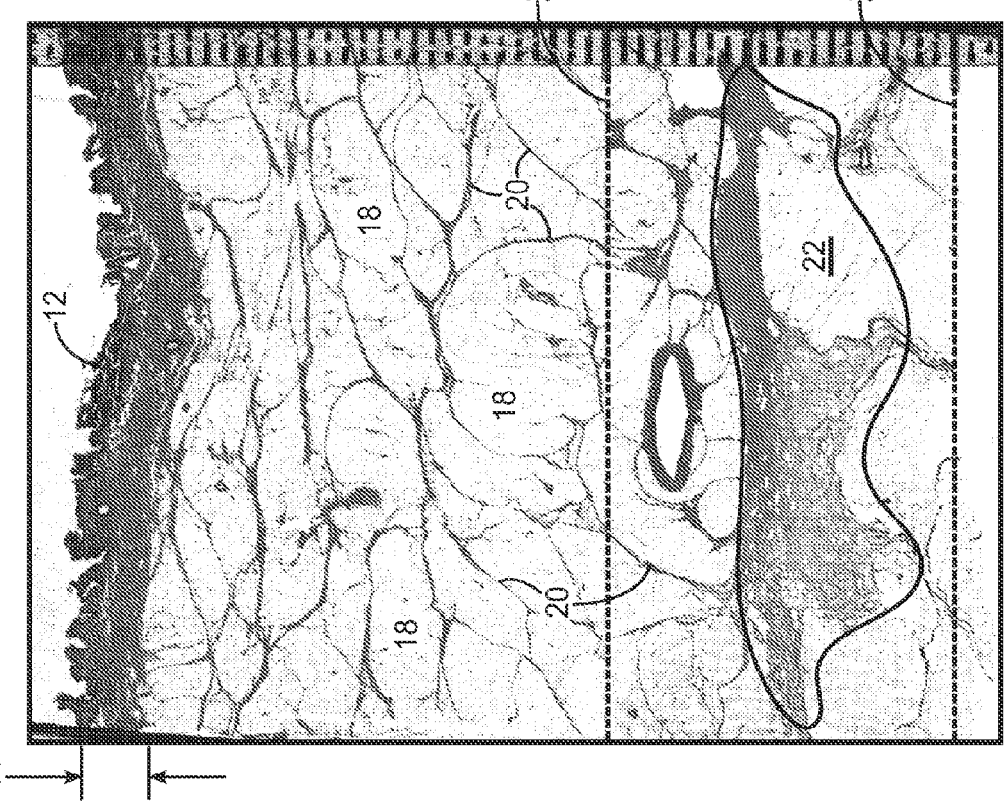

Proper utilization of the methods described herein can reduce the volume of a region of adipose tissue. Histology slides of tissue using the methods described herein are shown in FIGS. 12 and 13. These histology pictures show both the skin line 12 and skin layer 14 are undamaged. There is also shown a region of adipose tissue 16 having a relatively safe depth for this type of treatment. The treatment zone is found between the markers Z1 and Z2. Normal adipocytes (fat cells) 18 and normal collagen fibrils 20 are shown between the skin layer 14 and the treatment zone Z1. Within the treatment lines Z1, Z2 are shown two regions of heavy collagen population and nearly complete lack of adipocyte structures. The lesion field 22 shows both the collapse and destruction of adipose tissue and the denaturing of collagen fibrils which contract the tissue volume as the destroyed tissue mass is gradually removed from the body (through the body's natural wound healing response). The reduction of adipose tissue volume in this manner provides a similar long term result to liposuction. Since the tissue loss is gradual, there is no sudden looseness of the skin layer, nor skin deformation observed immediately after a patient undergoes a treatment using the methods described herein.

Review of the material disclosed herein will provide one skilled in the art with numerous alternative methods of accomplishing the desired objectives described, as well as methods not specifically mentioned herein. The description provided should be taken as illustrative and non-limiting, thus the present embodiments as well as alternative embodiments and equivalents are intended to be captured by the accompanying claims.

What is claimed is:

1. A method of modifying adipose tissue using high intensity focused ultrasound energy, the method comprising:
   determining a volume of adipose tissue to be treated;
   identifying a corresponding surface area of skin over the volume of adipose tissue;
   moving a therapy transducer on the surface area of skin; and
   applying multiple treatments of the high intensity focused ultrasound energy into a targeted volume of the volume of adipose tissue, each of the multiple treatments being insufficient to provide necrosed tissue cells and denatured collagen fibrils in the targeted volume, the combined multiple treatments being sufficient such that the necrosed tissue cells and denatured collagen fibrils are produced in the targeted volume, and an energy flux of the high intensity focused ultrasound energy into the targeted area of each of the multiple treatments is less than 35 J/cm$^2$,
   wherein moving the therapy transducer on the surface area of skin comprises, during the application of the multiple treatments, moving the therapy transducer to form a plurality of scan lines that overlap.

2. The method of claim 1 further comprising:
   marking the corresponding surface area of skin to create a plurality of guide markers at a predetermined spacing within the corresponding surface area.

3. The method of claim 1 wherein a temperature of the adipose tissue in the targeted volume is less than 37 degrees Celsius between consecutive treatments of the multiple treatments and is greater than 37 degrees Celsius after the multiple treatments are applied.

4. A method of modifying adipose tissue using high intensity focused ultrasound energy, the method comprising:
   determining a volume of adipose tissue to be treated;
   identifying a corresponding surface area of skin over the volume of adipose tissue;
   moving a therapy transducer on the surface area of skin;
   applying multiple treatments of the high intensity focused ultrasound energy into a targeted volume of the volume of adipose tissue, each of the multiple treatments being insufficient to provide necrosed tissue cells and denatured collagen fibrils in the targeted volume, the combined multiple treatments being sufficient such that the necrosed tissue cells and denatured collagen fibrils are produced in the targeted volume, and an energy flux of the high intensity focused ultrasound energy into the targeted area of each of the multiple treatments is less than 35 J/cm$^2$; and
   during the application of the multiple treatments, reducing a velocity at which the therapy transducer is moving.

5. The method of claim 4 wherein the adipose tissue in the targeted volume includes a lesion field at the focal zone of the therapy transducer and a halo field surrounding the lesion field, and applying the multiple treatments of the high intensity focused ultrasound energy further comprises:
   increasing a size of the halo field from the reduction in the velocity at which the therapy transducer is moving.

6. A method of modifying adipose tissue using high intensity focused ultrasound energy, the method comprising:
   determining a volume of adipose tissue to be treated;
   identifying a corresponding surface area of skin over the volume of adipose tissue;
   moving a therapy transducer on the surface area of skin;
   applying multiple treatments of the high intensity focused ultrasound energy into a targeted volume of the volume of adipose tissue, each of the multiple treatments being insufficient to provide necrosed tissue cells and denatured collagen fibrils in the targeted volume, the combined multiple treatments being sufficient such that the necrosed tissue cells and denatured collagen fibrils are produced in the targeted volume, and an energy flux of the high intensity focused ultrasound energy into the targeted area of each of the multiple treatments is less than 35 J/cm$^2$; and
   during the application of the multiple treatments, increasing a velocity at which the therapy transducer is moving.

7. The method of claim 6 wherein the adipose tissue in the targeted volume includes a lesion field at the focal zone of the therapy transducer and a halo field surrounding the lesion field, and applying the multiple treatments of the high intensity focused ultrasound energy further comprises:
   decreasing a size of the halo field from the increase in the velocity at which the therapy transducer is moving.

8. The method of claim 1 wherein the adipose tissue in the targeted volume includes a lesion field at the focal zone of the therapy transducer and a halo field surrounding the lesion field, and the halo fields of the scan lines overlap.

9. The method of claim 1 wherein the scan lines are aligned parallel to each other.

10. A method of modifying a targeted volume of adipose tissue in a patient using high intensity focused ultrasound energy, the method comprising:
    applying a set of one or more first treatments of the high intensity ultrasound energy into the targeted volume of the adipose tissue, the set of one or more first treatments subjecting the targeted volume to a cumulative first energy flux so that the set of the one or more first treatments does not cause a temperature of the adipose tissue in the targeted volume to exceed a predetermined temperature; and
    following the application of the set of the one or more first treatments, applying a second treatment of the high intensity ultrasound energy into the targeted volume of the adipose tissue, the second treatment subjecting the targeted volume to a second energy flux so that the combination of the cumulative first energy flux and the second energy flux causes the temperature of the adipose tissue in the targeted volume to exceed the predetermined temperature in order to produce a plurality of necrosed tissue cells and denatured collagen fibrils in the targeted volume,
    where the cumulative first energy flux of the one or more first treatments is less than 35 J/cm$^2$ and the second energy flux of the second treatment is less than 35 J/cm$^2$.

11. The method of claim 10 wherein the second energy flux is not greater than the first energy flux.

12. The method of claim 10 wherein the predetermined temperature is not greater than approximately 56 degrees Celsius.

13. The method of claim 12 wherein the predetermined temperature is not greater than approximately 46 degrees Celsius.

14. The method of claim 13 wherein the predetermined temperature is approximately 37 degrees Celsius.

15. The method of claim 10 wherein a pause in application of the high intensity focused ultrasound energy to the adipose tissue in the targeted volume occurs between the set of the one or more first treatments and the second treatment.

16. The method of claim 15 further comprising:
   during the pause, treating adipose tissue of the patient outside of the targeted volume with the high intensity focused ultrasound energy.

17. The method of claim 4 wherein moving the therapy transducer on the surface area of skin comprises, during the application of the multiple treatments, moving the therapy transducer to form a plurality of scan surfaces that overlap.

18. The method of claim 6 wherein moving the therapy transducer on the surface area of skin comprises, during the application of the multiple treatments, moving the therapy transducer to form a plurality of scan surfaces that overlap.

\* \* \* \* \*